United States Patent
Matveeva et al.

(10) Patent No.: US 9,526,779 B2
(45) Date of Patent: Dec. 27, 2016

(54) METHOD FOR CANCER IMMUNOTHERAPY AND PHARMACEUTICAL COMPOSITIONS BASED ON ONCOLYTIC NON-PATHOGENIC SENDAI VIRUS

(71) Applicant: Anna Senina, Salt Lake City, UT (US)

(72) Inventors: Olga Matveeva, Acton, MA (US);
Anna Senina, Salt Lake City, UT (US);
Vyacheslav Slav Mikhailovich Senin, Salt Lake City, UT (US)

(73) Assignees: Olga Matveeva, Acton, MA (US);
Anna Senina, SLC, UT (US)

( * ) Notice: Subject to any disclaimer, the term of this patent is extended or adjusted under 35 U.S.C. 154(b) by 0 days.

(21) Appl. No.: 14/438,545

(22) PCT Filed: Nov. 21, 2013

(86) PCT No.: PCT/RU2013/001043
§ 371 (c)(1),
(2) Date: Apr. 24, 2015

(87) PCT Pub. No.: WO2014/081346
PCT Pub. Date: May 30, 2014

(65) Prior Publication Data
US 2016/0022808 A1 Jan. 28, 2016

(30) Foreign Application Priority Data
Nov. 26, 2012 (RU) .................. 2012150147

(51) Int. Cl.
| | |
|---|---|
| *A61K 39/155* | (2006.01) |
| *A61K 39/00* | (2006.01) |
| *A61K 39/12* | (2006.01) |
| *A61K 9/00* | (2006.01) |
| *C12N 7/00* | (2006.01) |
| *C12N 7/01* | (2006.01) |

(52) U.S. Cl.
CPC .......... *A61K 39/155* (2013.01); *A61K 9/0019* (2013.01); *A61K 39/0011* (2013.01); *A61K 39/12* (2013.01); *C12N 7/00* (2013.01); *A61K 2039/515* (2013.01); *A61K 2039/5152* (2013.01); *A61K 2039/525* (2013.01); *A61K 2039/54* (2013.01); *A61K 2039/552* (2013.01); *A61K 2039/585* (2013.01); *C12N 2760/18834* (2013.01); *C12N 2760/18871* (2013.01)

(58) Field of Classification Search
CPC ................... C12N 2760/16121; A61K 35/768
See application file for complete search history.

(56) References Cited

U.S. PATENT DOCUMENTS

| | | |
|---|---|---|
| 7,871,765 B2 | 1/2011 | Kotani et al. |
| 8,691,212 B2 | 4/2014 | Kaneda et al. |
| 2002/0098576 A1 | 7/2002 | Nagai et al. |

OTHER PUBLICATIONS

Chang CY et al, Virus-stimulated neutrophils in the tumor microenvironment enhance T cell-mediated anti-tumor immunity. Oncotarget. May 31, 2016. doi: 10.18632/oncotarget.974.

Fujihara A. et al. Intratumoral injection of inactivated Sendai virus particles elicits strong antitumor . . . Cancer Immunol Immunother. Jan. 2008;57(1):73-84.

Gao H. et al, Induction of apoptosis in hormone-resistant human prostate cancer PC3 cells by inactivated Send . . . Environ Sci. Jul. 2014;27(7):506-14. doi: 10.3967/bes2014.08.

Hasegawa Y/ et al, Urokinase-targeted fusion by oncolytic Sendai virus eradicates orthotopic . . . Mol Ther. Oct. 2010;18(10):1778-86. doi: 10.1038/mt.2010.138.

Jiang Y. et al, Cytoplasmic calcium increase via fusion with inactivated Sendai virus induces apoptosis in human mult.. Oncotarget. Apr. 29, 2016. doi: 10.18632/oncotarget.9105.

Kaneda Y, A non-replicating oncolytic vector as a novel therapeutic tool against cancer. BMB Rep. Dec. 2010;43(12)773-80. doi: 10.5483/BMBRep.2010.43.12.773.

Kato T. et al, RIG-I helicase-independent pathway in sendai virus-activated dendritic cells is critical for preventing lung of AT6.3 prost . . . Neoplasia. Nov. 2012;12(11):906-1.

Kawaguch Y.et al,Efficient eradication of hormone-resistant human prostate cancers by inactivated Sendai . . . ,Int J Cancer. May 15, 2009;124(10):2478-87. doi: 10.1002/ijc.24234.

Kawano H. et al, A new therapy for highly effective tumor eradication using HVJ-E combined with chemotherapy. BMC Med. Sep. 21, 2007;5:28.

Kawano H. et al, New potential therapy for orthotopic bladder carcinoma by combining HVJ envelope with . . . Cancer Chemother Pharmacol. May 2008;61(6):973-8.

Saga K. et al, Systemic administration of a novel immune-stimulatory pseudovirion . . . Clin Cancer Res. Feb. 1, 2013;19(3):668-79. doi: 10.1158/1078-0432.CCR-12-1947.

Shibata S. et al, Induction of efficient antitumor immunity using dendritic cells activated by recombinant Sendai virus and its modula . . . J Immunol. Sep. 15, 2006;177(6):3564-7.

Takehara Y. et al, Anti-tumor effects of inactivated Sendai virus particles with an IL-2 gene . . . Clin Immunol. Oct. 2013;149(1):1-10. doi: 10.1016/j.clim.2013.05.019.

Tanaka M. et al. Sterile alpha motif containing domain 9 is involved in death signaling of malignant gliom . . . Int J Cancer. Apr. 15, 2010;126(8):1982-91. doi: 10.1002/ijc.24965.

Tanemura A. et al, Recent advances and developments in the antitumor effect of the HVJ envelope . . . Cancer Gene Ther. Nov. 2013;20(11):599-605. doi: 10.1038/cgt.2013.61.

(Continued)

*Primary Examiner* — Bao Li

(57) ABSTRACT

The invention relates to the field of immunology and medicine, more specifically, oncology, and can be useful for the treatment of patients with carcinomas and sarcomas. A pharmaceutical composition is provided which contains biologically active oncolytic Sendai virus strain Moscow PTA-13024, and a method of treating patients with said malignancies is developed including administration of the said composition to a patient's body. The strain Sendai-Moscow deposited into ATCC as frozen allantoic fluid (deposit PTA-13024) and as lyophilized form (deposit PTA-121432) is characterized by high oncolytic activity and safety for humans. The exploitation of the invention allows an increase in efficacy of treatment due to direct elimination of malignant cells via virus action and induction of anti-tumor immunity by viruses.

16 Claims, No Drawings

(56) References Cited

OTHER PUBLICATIONS

Tatsuta K. et al, Complete elimination of established neuroblastoma by synergistic action of gamma-irradiation . . . Gene Ther. Feb. 2009;16(2):240-51. doi: 10.1038/gt.2008.161.
Ueda Y. et al, Sendai virus for cancer immunotherapy. Methods Mol Biol. 2009;515:299-308. doi: 10.1007/978-1-59745-559-6_21.
Yoneyama Y. et al, Development of immunostimulatory virotherapy using non-transmissible Sendai virus-activated dendr . . . Biochem Biophys Res Commun. Mar. 30, 2007;355(1):129-35.
Yonemitsu Y. et al, Immunostimulatory virotherapy using recombinant Sendai virus as a new cancer therapeutic regimen. Front Biosci. Jan. 1, 2008;13:1892-8.
Zhang Q. et al, Inactivated Sendai virus suppresses murine melanoma growth by inducing host im . . . Biomed Environ Sci. Oct. 2012;25(5):509-16. doi: 10.3967/0895-3988.2012.05.003.
Kinoh H. et al, New cancer therapy using genetically-engineered oncolytic Sendai virus vector. Front Biosci. Jan. 1, 2008;13:2327-34.
Kinoh H. et al, Generation of optimized and urokinase-targeted oncolytic Sendai virus vectors . . . Gene Ther. Mar. 2009;16(3):392-403. doi: 10.1038/gt.2008.167.
Komaru A. et al, Sustained and NK/CD4+ T cell-dependent efficient prevention of lung met . . . J Immunol. Oct. 1, 2009;183(7):4211-9. doi: 10.4049/jimmunol.0803845.
Kurooka M. et al. Inactivated Sendai virus particles eradicate tumors by inducing immune responses through blocking regulatory T cells. Cancer Res. Jan. 1, 2007;67(1):227-36.
Liu L. et al, An RNA Molecule Derived From Sendai Virus DI Particles Induces Antitumor Immunity and Cancer . . . Mol Ther. Feb. 2016;24(1):135-45. doi: 10.1038/mt.2015.201.
Matsuda M. et al, Immunogene therapy using immunomodulating HVJ-E vector augments ant . . . J Neurooncol. May 2011;103(1):19-31. doi: 10.1007/s11060-010-0355-x.
Morodomi Y. et al, BioKnife, a uPA activity-dependent oncolytic Sendai virus, eliminates pleural spread of malig . . . Mol Ther. Apr. 2012;20(4):769-77. doi: 10.1038/mt.2011.305.
Nishikawa T. et al, Systemic administration of platelets incorporating inactivated Sendai virus eradicates mela . . . Mol Ther. Dec. 2014;22(12):2046-55. doi: 10.
Nomura et al, 13-Cis retinoic acid can enhance the antitumor activity of non-replicating Sendai virus particle . . . Cancer Sci. Feb. 2013;104(2):238-44. doi: 10.1111/cas.12063.
Okano S. et al, Provision of continuous maturation signaling to dendritic cells by RIG-I-stimulating . . . J Immunol. Feb. 1, 2011;186(3):1828-39. doi: 10.4049/jimmunol.0901641.
Zimmerman M. et al, Attenuated and protease-profile modified sendai virus vectors as . . . PLoS One. Mar. 5, 2014;9(3):e90508. doi: 10.1371/journal.pone.0090508. eCollection 2014.
Saga K. et al.Oncolytic Sendai virus-based virotherapy for cancer: recent advances. Oncolytic Virotherapy. 2015, vol. 4,pp. 141-147. doi:https://dx.doi.org/10.2147/OV.S6641.

METHOD FOR CANCER IMMUNOTHERAPY AND PHARMACEUTICAL COMPOSITIONS BASED ON ONCOLYTIC NON-PATHOGENIC SENDAI VIRUS

FIELD OF THE INVENTION

The present invention relates to the field of virology, immunology and oncology, more specifically, to providing pharmaceutical compositions for the treatment of carcinomas and sarcomas, and to the methods of these malignancies treatment. More particularly, the present invention relates to providing therapeutic pharmaceutical composition on the basis of Sendai virus strain deposited into ATCC as frozen allantoic fluid (deposit PTA-13024) and as lyophilized form (deposit PTA-121432), which is effective for the treatment of Human patients and animals with malignant diseases (carcinomas and sarcomas).

BACKGROUND

Metastatic cancer largely remains an incurable disease that requires development of novel therapeutic strategies. While the accumulating knowledge on molecular basis of cancer offers new potential targets for anticancer drugs, there is an alternative approach that relies on mechanisms developed through the millions of years of human co-existence with viruses. The viruses emerge as promising instruments against cancer. Substantial selectivity of infection and replication in cancer cells is characteristic of many viruses, and their therapeutic efficiency and safety can be improved by genetic manipulations, or by directed bioselection.

The idea of using viruses in the treatment of malignancies dates back to the beginning of the 20$^{th}$ century when reports on cases of spontaneous tumor regression after viral diseases or vaccination started to appear [1-6]. However, it took several decades of intense studies of the complex relations between viruses and their hosts until viruses started to be considered as potential tools for cancer therapy [7]. Modern studies on oncolytic viruses represent a dynamic and exciting field that absorbs the most recent discoveries in molecular, cell and cancer biology. Viruses can be quickly modified by recombinant DNA technology thereby rapidly incorporating the fast growing knowledge into oncolytic virus design. The studies involve a wide array of viral species belonging to diverse viral families, such as adenoviruses, herpesviruses, parvoviruses, enteroviruses, reoviruses, rhabdoviruses, paramyxo- and myxoviruses, alphaviruses, myxoma viruses and poxviruses. Examples of large randomized trials include phase III trial of an attenuated strain of herpes simplex virus-1 (HSV-1) that encode human granylocyte-macrophage colony-stimulating factor (GM-CSF) in the treatment of patients with metastatic melanoma [8]; phase II trial of reovirus in combination with chemotherapy in patients with head and neck cancer [9] and phase II trial of genetically engineered oncolytic poxvirus JX-594 in patients with hepatocellular carcinoma [10]. These trials confirm that oncolytic viruses do not produce substantial side effects and have a considerable antitumor efficacy affecting the overall patient survival.

Many members of the paramyxovirus family are now being considered as potential promising tools in cancer therapy. Among them Newcastle disease virus, Measle virus, Mumps Virus and Sendai Virus [11-13].

Sendai Virus

Studies of the anticancer effects of Sendai virus (SeV), which is also known as murine parainfluenza virus type 1 or hemagglutinating virus of Japan, are proceeding in several countries. The SeV virus belonging to the Respirovirusgenus is responsible for a highly transmissible respiratory tract infection in mice, hamsters, guinea pigs and rats [14]. It can be detected in mouse colonies worldwide. While SeV spreads in rodents through both air and direct contact routes [14], it is considered very safe for humans. One strain of SeV was approved in USA for a small human clinical trial for the prevention of a pediatric disease caused by parainfluenza type 1 virus. The trial demonstrated that the intranasal administration of SeV was well-tolerated and protecting against human parainfluenza virus infection[15].

Sendai virus has oncolytic properties. Genetically engineered recombinant Sendai virus (rSeV) disseminates extensively in human tumor cells xenotrasplanted to nude mice without spreading to the surrounding normal cells [16]. This dissemination leads to the inhibition of tumor growth in the mice. The tested tumor cells include fibrosarcoma, pancreatic epithelioid carcinoma and human colon carcinoma [16]. A significant reduction of tumor growth, including the complete elimination of established brain tumors, was demonstrated in murine models in a study using a different rSeV strain [17]. Similar results were obtained with mouse xenografts of human sarcoma and prostate cancer [16, 18]. Recombinant SeV efficiently eliminated tumors in rat models, including melanoma, hepatocellular carcinoma, neuroblastoma, squamous cell carcinoma and prostatic cancer [19].

Remarkably, the replication of SeV is not absolutely required for the oncolytic effects of SeV as even UV inactivated virus was shown to be efficient against colon[20, 21] renal[21] and prostate carcinomas in mouse models [22].

The UV inactivated virus with enhanced antitumor activity was constructed by conjugation of interleukin-12 with hemagglutinin-neuraminidase (HN)-depleted viral particles (HVJ-E). It was demonstrated that this novel immune-stimulatory pseudovirion suppresses lung metastatic melanoma growth by regionally enhancing IFN-gamma production without increasing the serum IFN-gamma level [23].

In all mentioned studies SeV eradicated the tumors or significantly inhibited their growth. No regular clinical studies with SeV have been carried so far, although the apparent safety of the virus and the promising preclinical data suggest that SeV could be an excellent candidate for oncolytic virotherapy. Supporting these hopes is a case of a short-term remission in a patient with acute leukemia following an intravenous injection of live SeV described back in 1964 [24].

Mechanisms of Viral Antitumor Activity

Oncolysis Mediated by Direct Killing During Selective Replication of Paramyxoviruses in Cancer Cells The cancer cells are generally better hosts for viruses than normal cells. Cancer cells usually acquire defects in the protective mechanisms that resist viral replication. This also relates to paramyxoviruses. The upregulation of p53 by IFNs plays protective role against the emerging cancer cells. Therefore, cancer cells experience strong selection pressure against both the p53 and the IFN-mediated mechanisms. During the malignant progression cancer cells acquire mutations in different components of the IFN system, p53 and apoptotic pathways that allow them to escape from the host regulation and to expand. But the very same defects that promote tumor growth provide the opportunity to destroy cancer cells with the use of oncolytic viruses.

Dissection of the general and specific mechanisms of complex interactions in viral oncolysis is important for designing new variants of oncolytic paramyxoviruses that would direct their potentials toward a more safe and efficient elimination of cancer cells through the direct killing and the stimulation of anticancer immunity. Studies on viral oncolysis mediated by paramyxoviruses have revealed several independent mechanisms that collectively contribute to their strong anticancer effects.

Role of Broken Innate Antiviral Defense Mechanisms in Cancer Cells

While pretreatment with the endogenous or exogenous IFN-beta completely inhibited replication of Newcastle Disease Virus (NDV) (a representative of Paramyxoviruses) in normal cells, no effect on viral replication was observed in tumor cells [25]. Similarly, while normal macrophages with intact IFN system were not susceptible to NDV infection, the macrophage-derived tumor cell lines showing low responsiveness to IFN-alpha and low expression level of IFN-beta were permissive for replication of the virus [26].

Cancer cells show defects in the IFN induction in response to NDV infection. Infection of several tumorigenic human cell lines with NDV showed a delayed response in the expression of antiviral genes such as PKR and MxA. While in non-tumorigenic peripheral mononuclear blood cells (PMBC) the replication cycle of NDV is stopped after the production of positive-strand RNA, it keeps going in tumor cells [27]. However, while the deficiency in IFN pathways is quite common in cancer, it cannot be regarded as a requirement for the increased sensitivity to viruses: some cancer cell lines show high sensitivity to killing by NDV even though they retain the responsiveness to IFN treatment [28, 29].

The replication of NDV in cancer cells results in death of infected cells. Efficient apoptosis was observed in a study involving 14 human cancer cell lines of ecto-, endo-, and mesodermal origin [28]. Although cancer cells infected with NDV eventually die, the apoptotic pathways are not necessarily fully intact in cancer cells. In fact, the increased sensitivity of cancer cells to virus infection is enforced by the attenuated apoptosis; it gives the cells enough time for successful viral replication and consequent viral spread. In a non-small-cell lung carcinoma cell line A549 that is relatively resistant to apoptosis due to overexpression of the anti-apoptotic protein Bcl-XL the oncolytic activity of NDV was significantly enhanced, even though the cells were capable of a robust type I IFN response[30]. In another study the overexpression of anti-apoptotic protein IAP Livin correlated with the enhanced oncolytic activity of NDV chemotherapy-resistant melanoma cells. These melanoma cells also demonstrate an intact IFN response [31]. The examples indicate that the increased sensitivity of cancer cells to viral infection can be achieved through different mechanisms that include defective IFN system, or compromised apoptotic response.

Formation of Syncytium Contributes to Viral Oncolysis

Some paramyxoviruses can achieve spreading of virus infection independent on the release of mature virus particles. The mechanism includes fusion of infected cells with their non-infected neighbors. The fusion results in the formation of a syncytium, a large polykaryonic conglomerate originating from many cells. For a single infected cell up to 50-100 neighboring cells may fuse together to form a syncytium[32]. The process of cell fusion allows the virus to avoid the likely exposure to host neutralizing antibodies. Usually the syncytia survive no longer than 4-5 days and it is unclear to which extent the apoptosis plays a role in their death. Experiments with caspase inhibitors suggest that apoptosis is not the only mechanism responsible for the fusion induced cell death [33]. It was proposed that the syncytia die through a processes that, by multiple morphological and biochemical criteria, bear very little resemblance to the classical apoptosis [34, 35].

It is likely that the ability of some viruses to induce the formation of syncytia may correlate with their oncolytic potential. The fusion protein of NDV was introduced into an oncolytic strain of vesicular stomatitis virus (VSV), which significantly enhanced oncolytic activity of the virus against multifocal hepatocellular carcinoma in the livers of immunocompetent rats [36]. Similarly, the oncolytic activity of a strain of replication-competent herpes simplex virus (HSV) was significantly increased after the introduction of a hyperfusogenic glycoprotein from the gibbon ape leukemia virus [37]. The fusogenic potential could be further increased by the introduction of amino acid substitutions. A novel NDV variant harboring an L289A substitution within the F gene possesses an enhanced fusion and oncolytic activities against rat hepatocellular carcinoma cells, both in vitro and in immunocompetent rats [38]. A mutant of SV5 paramyxovirus that harbors a glycine-to-alanine substitution in the fusion protein was hyper-fusogenic and displayed an enhanced oncolytic activity [39]. Remarkably, even plasmid vectors [30, 40, 41] or replication-deficient viruses [42-44] expressing the fusogenic membrane glycoproteins are capable of promoting significant tumor regressions, suggesting that the cell fusion may substantially contribute to the oncolytic activity of paramyxoviruses.

Oncolysis Mediated by the Virus-Induced Stimulation of the Antitumor Immune Response In addition to the direct killing of infected cancer cells viral infection elicits systemic responses that contribute to viral oncolysis.

Many viral and bacterial pathogens have a tendency to accumulate in the primary tumors and metastases, so viral particles concentration increases in tumor tissue. In short, such process can be called tumor xenogenisation. This term "xenogenisation" is a neologism. Pathogens bring into tumor mass a lot of biological non-self-material. This alien material is rich with foreign antigens that have immuno-triggering properties. The process can be called by new term derived from Greek "xeno" (meaning alien, stranger).

Appearance of foreign virus proteins in the infected cancer cells increases visibility of these cells by immune system.

The systemic response to viral infection includes stimulation of mechanisms of antiviral innate immunity, such as the production of IFNs, other cytokines and the activation of natural killers and T-lymphocytes. Also, viral infection elicits adaptive immune responses that not only act to contain the infection by targeting the released viral particles and the infected cells, but also assists in the exposure of cancer cells to the antigen-presenting cells leading to activation of the anticancer immune response.

Most tumors are MHC class I positive, but negative for MHC class II. MHC class I molecules are one of two primary classes of major histocompatibility complex (MHC) molecules, they are found on nearly every nucleated cell of the body. MHC class II molecules are secondary in two primary classes of major histocompatibility complex (MHC) molecules. They are expressed in professional, immune antigen presenting cells, such as dendritic cells but may also be induced on other cells including malignant by INF-gamma.

SeV is capable of INF-gamma stimulation that activates immunoproteasomes and triggers MHC class II production in cells, which are not in professional, immune antigen presenting cells, including malignant cells. IFN-gamma stimulates the expression of class I MHC molecules as well in many cells including malignant and it triggers production of co-stimulatory molecules on antigen presenting cells. This leads to extra antigen presentation of peptides from mutated-abnormal proteins produced in malignant cells. Consequently, malignant cells became more visible for immune system. IFN-gamma promotes the differentiation of naive helper T cells; it activates cytotoxic T cells and increases the cytotoxicity of NK cells. NK cells contain small granules in their cytoplasm with proteins such as perforin and proteases. Upon release in close proximity to a malignant cell, perforin forms pores in the cell membrane of the target cell, inducing either apoptosis or osmotic cell lysis. In addition IFNγ activates macrophages for phagocytosis and lysis.

Virus induced IFNs and cytokines stimulate dendritic cells (DCs) that educate cytotoxic T-lymphocytes to target tumor cells. When exposed to target malignant cells, cytotoxic T-lymphocytes release the cytotoxins perforin, granzymes, and granulysin that lead to cancer cell death. In addition viruses inside tumor mass might be covered by antibodies that in turn also could be detected by immune cells. Antibodies that bind to antigens can be recognized by receptors expressed on NK cells resulting in NK activation, release of cytolytic granules and consequent cancer cell destruction.

Some extra immune stimulation can occur because of host reaction to viral RNA even without viral infection, but after contact between host cell and non-pathogenic virus. There are immune system mechanisms that are sensitive to double stranded RNA (dsRNA). When the dsRNA is exogenous (coming from a virus particle with an RNA genome), the RNA is imported directly into the cytoplasm and cleaved to short fragments by the enzyme. RNA molecules shorter than about 25 nt largely evade detection by the innate immune system, which is triggered by longer RNA molecules. Most cells of the body express proteins related to the innate immune system, and upon exposure to longer than 25 n. RNA double stranded fragments of exogenous origin, these proteins initiate signaling cascades that result in inflammation. This inflammation might hypersensitize the malignant cells to immune system attack.

In theory, to some degree, anticancer immune activation can occur even without viral accumulation in tumor mass. Viral particles even being injected into skin and even being inactivated by antibodies can trigger some of the events described above.

Paramyxoviruses Stimulate the IFN Response

There is a considerable overlap in functions of innate and adaptive immune systems that protect against viral infection and against cancer. IFNs are glycoproteins secreted by cells in response to viral infection and helping neighboring cells to resist viral invasion. However, IFNs also have important functions in immunosurveillance and elimination of cancer cells [45, 46]. The released IFNs bind to their respective receptors and trigger signaling pathways that modulate broad biological responses including antiviral, growth inhibiting, immunomodulatory and pro-apoptotic [47, 48]. Among these responses IFNs limit viral spread by increasing the p53 activity and promoting apoptosis of the virus-infected cells.

Paramyxoviruses are known to be strong inducers of IFNs, the property that has been used in biotechnology: the Sendai Virus was chosen among many other viruses for industrial-scale production of IFN from human leukocytes [49]. In Human Peripheral Blood Leucocytes (HPBL) SeV behaves as a potent inducer of IFN-alpha [50], it induces the secretion of at least nine different IFN-alpha species [51]. In HPBL SeV also stimulates the production of IFN-gamma [52].Similarly, the NDV stimulates the production of IFN-alpha from several gene isoforms [53]. The induction of IFN can initiated following the recognition of dsRNA (particularly those containing 5'-triphosphates), which is synthesized during viral replication. The dsRNA is recognized by two types of pattern-recognition receptors, an endosomal TLR3 [54] and a cytoplasmic helicase RIG-1 [55, 56], which trigger the activation of transcription factor IRF3 controlling the expression of IFN genes. However, in HPBL the IFN secretion can be also induced by the FIN-protein a process independent of the dsRNA response [53, 57]. Apparently, the two alternative mechanisms of IFN induction explain the high interferon stimulating capacity of paramyxoviruses [57, 58].

IFNs exert complex systemic effects that make them useful means for adjuvant therapy of cancer [59, 60]. IFNs have been used in therapeutic schemes for the treatment of metastatic melanoma, renal carcinoma, Kaposi sarcoma, bladder carcinoma hairy-cell leukemia etc. The significant prolongation of a disease-free survival has now been largely validated by the combined analyses of multi-institutional trials and by the subsequent studies that have included meta-analyses [47]. IFNs exhibit strong antiproliferative and pro-apoptotic activities that might inhibit expansion of cancer cells and explain some of the therapeutic effects. INFs can act systemically by regulating the immune response through the activation of dendritic cells, cytotoxic T cells, and natural killer cells. IFNs markedly increase the MHC class I and class II-dependent antigen presentation that can cause increased presentation of tumor specific antigens by malignant and professional antigen presenting cells. This, in turn, can stimulate proliferation and antitumor activity of cytotoxic T lymphocytes.

The responses to IFNs are dysfunctional in many malignancies making the direct effects of IFNs less efficient. However, IFNs can affect tumor growth indirectly, through suppression of angiogenesis by altering the stimuli from tumor cells and by inhibiting endothelial cells. The degree of inhibition correlates with the reduced tumor vascularization and the consequent retardation of tumor growth [45, 47, 61]. The treatment with IFNs may also affect the viability of cancer stem cells that are highly resistant to chemo- and radiotherapy and are responsible for the disease relapses. Most likely, IFNs affect tumor vasculature and disrupt the vascular niche of stem cells, as it was found in mouse xenografts of human glioma [60].

Paramyxoviruses Stimulate Secretion of Cytokines

In HPBL SeV was shown to stimulate the synthesis of interleukins (IL) 2, 6, 8, macrophage inflammatory protein-1 alpha (MIP-1-alpha), MIP-1-beta, RANTES, and MCP-1 [50, 52]. Live or UV-irradiated SeV can stimulate the IL-6 release in the treated animals [20]. In dendritic cells the incubation with SeV results in the IL-6 secretion; the fusion protein (F) was found to be responsible for the effect [62]. The injection of the UV-inactivated SeV into established mouse renal cell carcinoma tumors resulted in the secretion of chemokine CXCL10 by infiltrating dendritic cells [21]. In a number of tested human tumor cells NDV was also shown to be an inducer of the CXCL10 secretion [63]. The CXCL10 was found to have an antitumor activity through the attraction of monocytes, macrophages, T cells, NK cells, and dendritic cells, the promotion of adhesion of T cells to endothelial cells, and the inhibition of angiogenesis [64]. In HPBL incubation with NDV also stimulates the secretion of cytokines TNF-alpha [65, 66] and TRAIL [53, 66]. It appears that the induction of TRAIL is due to a single viral protein FIN [53, 67]. In monocytes the NDV was also shown to induce the secretion of TRAIL, and to kill various human tumor cell lines following the stimulation of TRAIL-R2 receptors [67]. Macrophages could be also stimulated by incubation with NDV leading to up-regulation of a set of macrophage-specific genes and to secretion of TNF-alpha [68].

Stimulation of Natural Killer Cells by Paramyxoviruses

Natural killer (NK) cells constitute a type of cytotoxic lymphocytes that bridge the innate and adaptive branches of the immune system [69]. The NK cells participate in the early control against virus infection and in tumor immune surveillance. These cells have the ability to recognize the abnormal or stressed cells in the absence of antigen-specific cell surface receptors and MHC and destroy them, allowing a much faster protective effect. They do not require activation in order to kill cells that are not expressing "self" markers of MHC class I. Many viruses induce down-regulation of the MHC Class I molecules on the cell surface making the infected cells preferable targets for NK cells [70]. The NK cells widely interact with other components of the immune system affecting subsequent antigen-specific T and B cell responses [69].

The NK cells display natural cytotoxicity receptors (NCRs) responsible for their activation. Among these receptors are NKp46 and NKp44. It was found that the HN protein of paramyxoviruses directly interacts with the NCRs NKp44 and NKp46 and triggers the NK-mediated cells lysis [71-74]. Studies with the UV-inactivated SeV virus highlight the important role of NK cells in the virus mediated oncolysis. In a mouse renal cancer model the UV-inactivated SeV produced strong anticancer effect, which was compromised by co-injection of an NK-depleting anti-GM1 antibody [21].

Stimulation of Dendritic Cells

Dendritic cells (DCs) are professional antigen-presenting cells that can efficiently stimulate innate as well as adaptive immune responses against various pathogens and cancer cells. After sensing a virus or other pathogens, the DCs enter a maturation program and became competent for education of naïve T cells.

The UV inactivated SeV can cause extensive tumor infiltration by dendritic cells (DCs) [75]. The ex vivo infection of DCs by recombinant SeV can induce DCs maturation and activation in only one hour [76]. Treatment with activated DCs harboring different variants of recombinant SeV can improve dramatically the survival of animals inoculated with cells of malignant melanoma, neuroblastoma, hepatocellular, squamous cell, colon and prostate carcinomas [19, 77-80]. The administration of such DCs before tumor inoculation has demonstrated a preventive effect against lung metastasis of neuroblastoma [81] and prostate carcinoma [82]. Another response of DC cells to virus infection is inhibition of immunosuppression mediated by the regulatory T-cells. In experiments with the UV-inactivated SeV it was found that carbohydrates of the viral F-protein are recognized by an unknown receptor(s) on DC cells leading to the NF-kappa B activation and secretion of IL-6 [75].

Role of Tumor Specific Cytotoxic T-Cell Mediated Activity

Infection of tumor cells with NDV can stimulate the tumor-specific cytotoxic CD8+T-cell (CTL) response and increase the CD4+T-helper cells' activity even in the absence of an antiviral T-cell response [83]. The activation and infiltration of tumor sites with CTLs is the result of complex effects of viral infection on the immune system, including local and systemic release of IFNs and other cytokines. Localized inflammation associated with the in situ cytokine production may contribute to the anti-tumor response [84]. Interestingly, the UV-inactivated virus was as active in promoting the tumor-specific CTL response as the infectious NDV. It was found that this effect is mediated by the presence on the tumor cell surface of functional viral 1-1N molecules that have affinity to plasma membranes and therefore can mediate a strong adhesion of the infected cells to CTLs [83]. Since the 1-1N proteins of SeV and NDV are highly homologous, the data suggest that the 1-1N protein, regardless of whether it derives from SeV, NDV or other related paramyxoviruses, can activate both NK and CTL responses.

Role of Viral Sialidase Activity of the HN Protein in Paramyxovirus Oncolysis

Sialic acids represent N- or O-substituted derivatives of neuraminic acid, a monosaccharide with a nine-carbon backbone found in several classes of cell surface and secreted glycan molecules. The sialic acids provide the hydrophilicity to vertebrate cell surfaces, and act as receptors for certain pathogens and toxins. The sialic acids play important structural roles, as they bind selectins, components of intracellular matrix. Metastatic cancer cells often express a high density of sialic acid-rich glycoproteins that increase the invasive potential. The overexpression of sialic acid on the surfaces creates a negative charge on cell membranes, leading to repulsion between cells that promote metastases by helping cancer cells' entry into the blood stream [85, 86]. In a mouse model it was found that the ability of tumor cells to metastasize from subcutaneous sites depends on the abundance of sialic acids [87]. In a model of non-invasive revertants of a highly metastatic mouse T-cell lymphoma the metastatic potential was lost coincident with the loss of sialylation[88]. A similar effect was observed for a Friend Leukemia cell line[89], in models of T-cell hybridoma, [90] melanoma [91] and colon carcinoma [92]. The extent of cell surface poly-sialylation was suggested as a marker characterizing the differentiation status of thyroid and small-cell lung carcinoma cells [93].

A more detailed analysis revealed qualitative differences in sialic acids on the surface of cells displaying different degrees of invasiveness. While in normal human colon cells, as well as in adenomas and several carcinomas of different grades an alpha2,3-linked sialic acid was detected, in the highly malignant variants alpha 2,6-linked sialic acids were also present. It was found that the malignant progression was associated with the de novo expression of an alpha 2,6 sialyl-transferase, which transforms the alpha 2,3-linked sialic acid into the 2,6-linked sialic acid [94]. The increase in alpha 2,6 sialylation coincident with tumor progression was also detected for hepatocellular carcinomas [95] and in colon adenocarcinomas [96-99].

Treatment with inhibitors of the sialylation process was shown to decrease the malignancy of cancer cells. Soyasponin I, a potent 2,3 sialyltransferase inhibitor, can diminish the metastatic and invasive properties of breast cancer [100] and melanoma cells [101]. A derivative of lithocholic acid that is also an inhibitor of sialyl transferase can reduce the metastatic potential of lung carcinoma cells [102].

One of the possible mechanisms linking the increased sialylation with malignant phenotype is the creation of a thick "coat" on the cell surface that hides cancer antigens and provides an escape of malignant cells from the immunosurveillance. For example, it was found that the tumor specific Lewis antigen of malignant medullary thyroid cancer can be masked from the immune system by both alpha 2,3- and alpha 2,6-linked sialic acid residues [103]. Removing some sialic acid residues from the surface of malignant cells by sialidase can unmask cancer specific antigens and make cells visible to the immune system.

The removal of sialic acids from tumor cells was associated with the reduced growth potential. Cytotoxic activity of NK cells was found to be dependent on sialic acids on the surface of tumor cells. Removal of sialic acids by sialidase resulted in the activation of NK cells and secretion of IFN-gamma [104].

The FIN proteins present in SeV, NDV and some other paramyxovirus exposes both erythrocyte agglutinating and neuraminidase (sialidase) activities [105, 106] Neuraminidase cleaves sialic acid on the cell surface [107]. These viruses use sialic acid-containing receptors on the cell surface to penetrate into cells due to the affinity of viral neuraminidase to sialic acid. The abundant presence of sialic acids on the surface of cancer cells can promote the preferential association of the virus with malignant rather than with normal cells and additionally contribute to the selective cytolytic effect in tumors and in the metastases. In particular, the above explanation for tumor selectivity was suggested in a study demonstrating high sensitivity to the SeV mediated lysis of sialic acid-rich prostate carcinoma cell lines PC3 and DU145 in comparison with normal prostate epithelium[22].

It was found that viral neuraminidase can remove sialic acid residues from the surface of malignant cells [106, 108] leading to a dramatic compromise of the ability of B lymphoma cells to induce T-cell activation[108]. The enzyme of NDV can cleave alpha 2,3-, alpha 2,6-[109] and alpha 2,8-linked sialic acid residues [110]. There appears no major difference in the cleavage substrate specificity in vitro for sialidases from NDV, SeV and Mumps viruses [111] suggesting that the ability to remove sialic acids from the surface of infected cells is attributed to all three members of the paramyxovirus family that demonstrate oncolytic activities. However, it is yet to be studied to what extent the ability of viruses to remove cell-surface sialic acids contributes to improvement of immunosurveillance and to the virus-specific oncolysis.

Thus, a number of mechanisms could explain oncolytic effect of Sendai virus. The oncolytic potential might depend on the individual characteristics of the strain. The virus can directly kill cancer cells replicating in them. SeV particles induce the formation of cell syncytium. The cells fused into a syncytium can no longer divide and are doomed to collective synchronous death. Furthermore, the virus causes immune-mediated killing of malignant cells, which occurring due to a strong activation of NK, as well as by potentiating the antitumor activity of cytotoxic T-cells and antigen-stimulated dendritic cells. The viral neuraminidase can provide high specific affinity for the virus to sialic acid polymer, frequently present in excess in the membranes of malignant cells. This increases the specific affinity of the virus to the malignant cells versus normal cells.

DESCRIPTION OF THE INVENTION

In the mid-1950s an academician in the Academy of Medical Sciences (AMS, USSR), V. M. Zhdanov, received a Sendai virus strain from Japan that was used later as a model pathogen in the Institute of virology named after D. I. Ivanovsky (the Russian Academy of Medical Sciences, RAMS) (84)(85)(86). In the late 1960s the inventors received this strain from the laboratory headed by V. M. Zhdanov, and it was designated as "Moscow strain". There were about 30 passages of the strain performed later in chicken eggs at the laboratory of the USSR Blochin Cancer Research Center of AMS. Prolonged passaging of virus in cultured cells or tissues is known to result in virus modification in many cases. Many of the currently known vaccine strains were obtained this way. In this case the prolonged passaging of the virus Sendai Moscow strain led to production of a modified variant. Its high safety for humans and animals made it a prospective agent for use in the therapy of human patients and animals with malignant tumors.

The inventors developed a pharmaceutical immunogenic composition composed on the basis of purified isolated biologically active virus, and a method for treating patients with malignant solid tumors or in need of immunotherapy against metastasis via administration of the said composition. If the composition further includes cells obtained from patient's tumor tissues, additional therapeutic effect is achieved due to enhancement of immunological response to autologous tumor cells by the virus.

In a preferred embodiment the composition should include viable virus. But the virus can be prior inactivated with ultraviolet radiation before being added to the composition. The virus can be propagated in chick embryos, or it can be adapted for the propagation in a cell culture. The virus can be an original strain or genetically engineered construct developed on the basis of Sendai virus. The viral material can be collected from allantoic fluid or cell culture medium. The virus can be added to the composition either in the form of suspension in allantoic fluid or in lyophilized form. Pharmaceutically acceptable carriers for the use in the composition of the present invention include normal saline or aqueous buffers, such as PBS, and the like. Further, the composition of the present invention can include other additives, such as adjuvants, stabilizers, antioxidants, and the like.

The virus is administered to a patient's body in a purified form as a part of the pharmaceutical vaccine composition in combination with normal saline or other pharmaceutically acceptable carrier. The composition can be administered to the body in different ways, more particularly, intradermally, subcutaneously, intramuscularly or intratumorally. The more preferable way is intratumoral administration. The virus can be present in the composition either in native or in inactivated form. The composition can either include the virus in combination with X-ray inactivated cells obtained by dispersion of patient's tumor tissues. Additionally, the composition can be administered to a patient's body in combination with X-ray inactivated cells obtained from immunogenic tumor cell lines The composition can be administered to a patient's body in combination with chick embryo cells, whereby additional virus replication being possible in chick embryo cells inside a patient's body, that enhances its therapeutic action.

The method of treatment includes at least one administration to a patient of an effective amount of the composition according to the invention. In a preferred embodiment the immunotherapy course includes 12 injections of the vaccine composition. The injections are administered with 7-10 day intervals. Preferably, injectable material is administered as small doses. For example, if administration of 1 mL of the composition into a tumor is needed, the administration is preferably performed in 10 points with 100 micro liters aliquots to achieve a maximally uniform distribution of the virus inside the tumor.

The method of treatment disclosed in the invention was successfully used in practice in Moscow and St. Petersburg in 1980-1990s for the management of oncologic patients with solid tumors (carcinomas and sarcomas). There is a Conclusion presented in the supplement on the results of the combined surgical and immunological treatment of oncologic patients with stage III or IV solid tumors in St. Petersburg City Clinical Hospital #26. After the surgery all the patients underwent immunotherapy course according to the method of the present invention for 3-4 months. Oncological disease-free survival was reported in 11 of 12 (92%) patients after radical surgery and in 4 of 15 (27%) patients after tumor reduction surgery.

Currently the strain Sendai-Moscow disclosed in the invention is deposited into ATCC culture collection for the purposes of patent procedure, in frozen allantoic fluid form PTA-13024 and in lyophilized form PTA-121432.

EXAMPLES

Protocol Examples

1. Viral Growth Protocol

For Sendai virus growth a standard technique for virus propagation in the amniotic cavity of embryos in fertilized chicken eggs is used The virus was grown in Specific Pathogen Free (SPF) fertilized chicken eggs. The virus intended for the injections to patients was checked for sterility.

On Day $7^{th}$ of embryo development a fertilized egg was inoculated with viral material. To provide aseptic conditions, the shell was sterilized with 70% ethanol, and then a hole was made in the shell of the egg for injecting 100 micro-liters of viral material into allantoic fluid with a syringe. After the inoculation of the virus into the egg the hole was sealed with melted wax. Incubation of the infected eggs was performed at 37.5° C. for 3 days. After the incubation, allantoic fluid was collected from the eggs with a syringe through a window in the shell. The yield was about 3 mL of allantoic fluid per each egg. The allantoic fluid was centrifuged for 10 min at 1000 g and 4° C. to get rid of solid particles, and then aliquoted. The allantoic fluid with suspended viral material was stored at −80° C. Part of the viral preparation was lyophilized. The lyophilized material can be stored at −20° C. The titer of the lyophilized part of the preparation is typically from 6 to 7, and that of non-lyophilized part—from 7 to 8 of Embryo Infectious Dose 50% ($EID_{50}$) per mL.

2. Preparation of Chick Embryos for Additional Virus Replication Inside a Patient's Body 2-5 Day old chick embryos are aseptically collected and dispersed first by dissecting with scissors and then by pipetting in normal saline supplemented with 10% serum and antibiotics: penicillin (100 IU/mL) and streptomycin (100 ug/mL) (P/S). In case of preparing suspensions of chick embryo cells for future use DMSO should be added to the suspension followed by temperature controlled freezing according to a standard protocol. The suspension is stored as aliquots in liquid nitrogen or at −130° C. All the manipulations with chick embryo cells after unfreezing should be performed in a cooling chamber and/or in an ice bath. To get rid of DMSO the content of the unfrozen aliquot tube is diluted 10-fold with full normal saline supplemented with 10% serum and P/S followed by centrifugation. Upon washing the cells are resuspended in 1 mL of allantoic fluid containing Sendai virus, and incubated for 30 min in an ice bath for virus absorption on the surface of the cells. The composition obtained is administered to a patient intradermally, at several sites, in amount of about 100 micro-liters per site. All the cells prepared from 2-3 embryos should be used for one injection.

If patient's tumor tissues are available after surgery, the embryonic cell suspension is mixed with the tumor cell suspension. This suspension should be prepared beforehand by dispersing the cells from the tumor material. About 5 to 20 million of tumor cells are needed for one injection.

3. Preparation of Dispersed Tumor Material for Vaccination

Following the surgery, the tumor material is divided into 2 parts. One part is used for histopathology, and the other part is stored at 4° C. in culture medium or full normal saline, supplemented with 10% serum and P/S for further preparation of material for vaccination. It is extremely desirable to perform further preparations of the tumor during the first several hours after the surgery. There are about 1 billion cells in 1 gram of tumor material, but this value can vary across a wide range for different tumors.

For autologic vaccine preparation the tumor material is mechanically dispersed followed by enzymatic treatment. The tumor is dissected with sterile sharp scissors to pieces 2-3 mm in size, in a Petri dish. The tumor fragments obtained are treated with enzymes. For this purpose a solution containing 0.2% collagenase and 10 mg/mL DNase in complete medium supplemented with 10% serum (full normal saline can be used instead of medium) and P/S is added to tumor material dissected with scissors. The resulting mixture is incubated for 15 min at 37° C. or overnight at 4-8° C. After the incubation with the enzymes, the material is slowly and carefully pipetted to achieve cell disintegration. After the pipetting the mixture is centrifuged for 1 min at 1000 g to remove incompletely dispersed pieces of the tumor. This can be also performed by filtration of the cell suspension through nylon net with pore size of 40 micron. After the removal of poorly dispersed pieces of the tumor, pronase (0.1%) and DNase (10 mg/mL) are added to the cell suspension for dead cell digestion. During a short incubation pronase digests dead cells, but with longer incubation, it starts to digest live cells, so, the pronase treatment must be very short. The suspension is incubated with the enzymes for 2 min at room temperature, and then centrifuged with cooling for 5 min to precipitate the cells. After centrifugation the cells are resuspended in complete medium supplemented with 15% serum and 10% DMSO. Upon the addition of DMSO, the cell suspension is frozen at a controlled rate of freezing according to a standard protocol. The suspension is stored as aliquots in liquid nitrogen or at −130° C. Washing-out of DMSO from the cells is performed with a 10× volume of cultural medium or full normal saline, supplemented with at least 10% serum and P/S. To inactivate the cell's proliferative ability, the cells are irradiated with gamma-rays (200 Gy). The cells can be irradiated either before or after the freezing, in the latter case the cells are transported to the source of radiation in dry ice and are irradiated while frozen. Cell viability after the dispersion process is assessed with trypan blue dye solution. Five to ten million of live tumor cells are needed for one vaccination.

4. Estimation of the Immune Reaction to Autologic Cancer Cells Developing Concomitantly with the Vaccination To estimate the immune reaction to autologic cancer cells developing concomitantly with the vaccination, the delayed-type hypersensitivity reaction was used. For this purpose gamma irradiated tumor cells (200 Gy) without virus were administered to patients. Following 24 hours post injection, the diameter of erythema appearing after administration of the cells, was measured. The reaction was considered to be positive where the erythema diameter exceeded 7 mm. While the number of the vaccinations increases for each patient, and in accordance with the regular stimulation of the immune response to cancer cells, the erythema should increase in size.

Examples of Clinical and Veterinary Use

Example 1

Medical Assessment Report on Surgical Treatment Combined with Immunotherapy of III-IV Stage Cancer Patients Issued to Chief Researcher at the Cancer Research Center of the Russian Academy of Medical Sciences, V. M. Senin, MD. PhD in Medical Science This assessment report presents results of monitoring cancer patients with solid tumors who were admitted to the Thoraco-Abdominal Department of the St. Petersburg City Hospital No. 26 in incurable and inoperable condition according to information from other hospitals.

Surgical and subsequent immune treatment took place from 02.95 to 04.96. During this time 27 patients with various tumor localizations and various histopathologies underwent surgery. Approximately half of the patients underwent radical surgery involving removal of the primary tumor and all found metastatic lesions. The other half underwent mitigating surgeries, with maximum tumor reduction. After surgery all patients completed a 3-4-month long course of immunotherapy using autologous cancer vaccines modified by V. M. Senin.

The following results were found after one year of observation. Disease-free survival was observed in 11 out of 12 patients (92%) following radical surgery.

Disease-free survival was observed in 4 out of 15 patients (27%) following tumor reducing surgeries.

Such findings significantly differ from historical and synchronous control data and testify to the significantly high efficiency and promise of the after-surgical immune therapy using auto-vaccines, taking into account the incurable and inoperable condition of these patients prior to the beginning of the surgical and immune treatment.

Dec. 20, 1996
Head Physician of the
St. Petersburg City Hospital No. 26 [Signature]
Honoured Doctor of Russia E. S. Zheleznyak
Hospital Senior Surgeon, Doctor of Medical Science, Professor
Thoracic Surgery Department Chairman at the
Medical Academy of Postgraduate Education [Signature] V. A. Tarasov
Head of the Hospital
Thoraco-Abdominal Department [Signature] V. V. Stavrovietsky
[round seal: St. Petersburg Healthcare Committee
St. Petersburg City Hospital No. 26]
Appendix to the Medical Assessment Report on Surgical Treatment Combined with Immunotherapy of III-IV Stage Cancer Patients Patients after Radical Surgeries 1) P. A. S., born 1914, record No. 26621. Rectosigmoidal carcinoma of large intestine, IV stage, $T_4N_2M_0$. Tubular differentiated adenocarcinoma with invasion to all layers of intestinal wall. Surgery date: Dec. 4, 1995. Results in 1 year and beyond=1 (see note)
2) V. M., born 1954, record No. 23974, thyroid gland carcinoma with metastases to the lungs. IV stage. Solid medullary carcinoma with stroma amyloidosis. $T_4N_3M_1$. Surgery date: Oct. 30, 1995. Results=1.
3) M. N. P., born 1940, record No. 2624. Retroperitoneal tumor 30×40×20 cm. Low-differentiated adrenocortical carcinoma with abdominal metastases. IV stage. $T_4N_1M_1$. Surgery date: Feb. 15, 1996. Results=1.
4) N. V. T., born 1962, record No. 24176. Peripheral adenocarcinoma of left lung, III stage. $T_4N_3M_0$. Surgery date: Oct. 16, 1995. Results=1.
5) V. A. G., born 1937, record No. 25882. Rectosigmoidal carcinoma of large intestine with mesenterium metastases. IV stage. Papillary carcinoma with invasion to intestinal wall. $T_3N_1M_0$. Surgery date: Nov. 29, 1995. Results=1.
6) L. I. P., born 1930, record No. 26620 Infiltrative peripheral carcinoma $B_6$ of left lung, III stage. Low-differentiated epidermal carcinoma. $T_3N_0M_0$. Surgery date: Dec. 7, 1995. Results=1.
7) M. Y. R., born 1925, record No. 13277. Low-differentiated cardia carcinoma, IV stage. $T_4N_1M_0$. Surgery date: Jun. 21, 1995. Results=1.
8) N. D. S., born 1953, record No. 22237. Solid tubular pleural mesothelioma, malignant. $T_4N_2M_0$. Surgery date: Oct. 11, 1995, Results=1.
9) N. P. S., born 1934, record No. 4757 Infiltrative carcinoma of left mammary gland with metastases to lymph nodes. $T_3N_2M_0$. Surgery date: Mar. 6, 1995. Results=1.
10) M. G. A., born 1978, record No. 1336. Synovial angiosarcoma of left ankle. $T_2N_0M_0$. Surgery date: Jan. 19, 1996. Results=1.
11) D. M. B., born 1941, record No. 21590. Low-differentiated rectal carcinoma, IV stage, $T_3N_2M_1$. Surgery date: Sep. 29, 1995, Results=1.
12) T., Carcinoma of distal bronchus of right lung, $T_2N_2M_0$, Surgery date: Results=3.

Patients, Surviving after Tumor-Reductive Surgical Procedures

1) V. M. D, born 1930, record No. 354. Solid tubular hyper-nephroid carcinoma of left kidney with metastases to prescalenic lymph nodes on the left. Clear-cancer cell metastases. IV stage. $T_3N_1M_1$. Surgery date: Dec. 18, 1995. Results=2.
2) G. M. V., born 1948, record No. 25310. Infiltrative carcinoma of pancreas head. $T_2N_1M_0$. Surgery date: Mar. 30, 1995. Tumor not removed. Anastomosis applied. Results=2.
3) A. N. N., born 1932, record No. 15130 Infiltrative adenocarcinoma of right mammary gland. III stage. $T_4N_2M_0$. Surgery date: Jul. 12, 1995. Results=2.
4) U. (outpatient). Myxoma of abdominal cavity. $T_4N_1M_1$. Surgery date 4.95. Results=2
Surgery performed at the Burdenko Hospital in Moscow Note Explanation of the Digital Notation of Results 1—There are currently no symptoms of malignancy
2—The process has stabilized. There are no symptoms of disease progress or of tumor regression
3—Backset. Fatal case.
Senior Surgeon of St. Petersburg City Hospital
No. 26, Doctor of Medical Science, Professor [Signature] V. A. Tarasov
Head of the Hospital
Thoraco-Abdominal Department [Signature] V. V. Stavrovietsky

Example 2

Case 1

Patient V. K., male, YOB 1922. In 1989 was diagnosed with prostate adenocarcinoma. Multiple metastases including a lesion in L1 with vertebral compression were detected. The patient was completely immobilized for 3 months due to severe pain in spine, pelvic bones and right ankle. He was prescribed narcotics for pain and was released from a hospital for symptomatic home care. The patient received Sendai virus immunotherapy from February 1989 through May 1989. Three months later pain was gone and the patient was evaluated at Blokhin Cancer Research Center (Moscow, modern Russia, and former USSR). Neither primary tumor, nor metastases were detected. However, X-ray showed remaining L1 vertebral destruction. The patient is pain free and tumor free in 2013. No malignancy!

Case 2

Patient L. Z., female, YOB 1929. In 1991 was diagnosed with right mammary gland carcinoma. In 1992 radical mastectomy was performed. In 1992 soon after surgery multiple metastastases in the operation scar and surrounding skin were detected. They merged together in solid growth. The patient refused chemotherapy and was released from a hospital for symptomatic home care. She received two cycles of Sendai virus immunotherapy in 1992. All visible metastases disappeared and the patient remained tumor free after immunotherapy for five years of observation.

Case 3

Patient L. F., female, YOB 1941. In July 1991 was diagnosed with undifferentiated ovarian adenocarcinoma. Both hysterectomy and oophorectomy were performed. Small bowel obstruction that developed after surgery was treated by colostomy. While performing laparotomy adhesions in the pelvis with several large metastases up to 5 cm were found. One of them grew in the lumen of the small intestine. The patient refused chemotherapy and was released from a hospital for symptomatic home care. She received one cycle of Sendai virus immunotherapy in 1992. All visible metastases disappeared and the patient remained tumor free after immunotherapy for five years of observation.

Case 4

Patient N. Zh., female, YOB 1939. (Medical Doctor herself). In early 1986 multiple malignant tumors with infiltrative growth in left breast were detected. In October of 1986 patient underwent radical mastectomy. In February 1991 growing metastases in the scar were found. At the same time metastastic lesion was also detected in left femur diaphysis. The patient started to receive a first cycle of Sendai virus immunotherapy in 1991 and underwent further X-ray testing simultaneously. Tests in October 1991 revealed metastases in frontal skull bones, the left parietal bone, in left iliac bone and in left sacroiliac joint. The patient refused suggested hormone therapy. Instead she received the second cycle of Sendai virus immunotherapy from October 1991 through February 1992. X-ray testing performed in December of 1993 in Blokhin Cancer Research Center (Moscow, modern Russia, and former USSR) showed the absence of lesions in all previously affected bones with exception of frontal bone metastasis. This lesion was still partially visible. However, it was not detected later. The next X-ray in 1997 showed no signs of metastases in patient's bones. The patient remained tumor free after immunotherapy for five years of observation.

Case 5

Patient I. M., male, YOB 1940. The patient was diagnosed with rectal adenocarcinoma. In 1992 the patient got radiotherapy and in May 1992 he was subjected to radical surgery. During laparotomy ascites and multiple metastases were found. They were located in regional lymph nodes, peritoneum and liver. The patient underwent Sendai virus immunotherapy cycle. After immunotherapy he suffered from bowel obstruction and was subjected to new surgical treatment. During the laparotomy no signs of metastatic lesions or ascites were found. Scars were detected on the lower surface of patient's liver. The patient remained tumor free after immunotherapy for five years of observation.

Example 3

Case 1

Dog Lyusya (born in 1993). A radical surgery was performed in 2004: mastectomy of all the mammary glands was done due to multiple tumors. Histopathology showed the tumors were tubular adenocarcinomas. One month later postoperative examination of the dog showed two new growing tumor nodes. One node was located inside the sutural scar in the area of the thorax (about 1 cm in diameter), another one—in a lymph node in the inguinal region (about 1 cm in diameter either). The decision was made to use Sendai-Moscow virus for treating these metastatic neoplasms. After 3 intratumoral injections of the viral material the metastatic neoplasm located inside the sutural scar dissolved. After 9 subcutaneous injections of the viral material to the inguinal region, where the lymph node metastasis was located, that metastatic neoplasm dissolved either.

In the same animal an extremely fast growing interdigital tumor (III-IV) was diagnosed on the right foreleg in 2006. The tumor grew from 3 mm to 1.5 cm in one and a half months. Aspiration biopsy demonstrated that the tumor contained malignant labrocytes and was low-differentiated. It was suggested to ablate the foreleg, as prognosis for the long-term survival of the animal was poor without such a radical surgery. Injections of the viral material helped to cause the stabilization of the fast-growing tumor in that dog. The tumor stopped growing after the first injection of the virus, however, the following 12 injections failed to cause its disappearance. Aspiration biopsy demonstrated again that the tumor contained malignant mast cells and was low-differentiated, so the decision was made to perform surgery. In two weeks after a partial surgical ablation followed by 1 administration of the viral material into the operative suture, the residual part of the tumor regressed.

Example 4

Case 2

Dog Ali (born in 2001). The animal had a slow-growing tumor. The tumor was revealed on the brachium in November 2007. To February 2009 the tumor doubled in size and reached about 5 cm in diameter. Aspiration biopsy demonstrated that the tumor was a fibrosarcoma. Injections of the Sendai-Moscow virus administered from March to May 2009 helped to cause initial stabilization of tumor growth, and then its regression. Ten injections of the virus were performed in total, in about three months after the first injection of the virus the tumor started decreasing in size slowly. It decreased to 1 cm in another three months, to the end of August. Moreover, a new aspiration biopsy test from multiple spots revealed no malignant cells.

REFERENCES

1. Dock, G., *The influence of complicating diseases upon leukemia*. Am J Med Sci, 1904. 127: p. 563-592.
2. De Pace, N., *Sulla scomparsa di un enorme cancro vegetante del collo dell'utero senza cura chirurgica*. Ginecologia, 1912. 9: p. 82-89.
3. Levaditi, C. and S. Nicolau, *Vaccine et neoplasmes* Ann Inst Pasteur 1923. 37 p. 443-447.
4. Farber, S. and L. K. Diamond, *Temporary remissions in acute leukemia in children produced by folic acid antagonist, 4-aminopteroyl-glutamic acid*. N Engl J Med, 1948. 238(23): p. 787-93.
5. Svejda, J., [*Viruses and tumors*]. Lek List, 1950. 5(23): p. 688-9.
6. Moore, A. E., *Effects of viruses on tumors*. Annu Rev Microbiol, 1954. 8: p. 393-410.
7. Kelly, E. and S. J. Russell, *History of oncolytic viruses: genesis to genetic engineering*. Molecular Therapy: The Journal of the American Society of Gene Therapy, 2007. 15(4): p. 651-659.
8. Senzer, N. N., et al., *Phase II clinical trial of a granulocyte-macrophage colony-stimulating factor-encoding, second-generation oncolytic herpesvirus in patients with unresectable metastatic melanoma*. J Clin Oncol, 2009. 27(34): p. 5763-71.
9. Karapanagiotou, E. M., et al., *Phase I/II trial of carboplatin and paclitaxel chemotherapy in combination with intravenous oncolytic reovirus in patients with advanced malignancies*. Clin Cancer Res, 2012. 18(7): p. 2080-9.
10. Heo, J., et al., *Randomized dose-finding clinical trial of oncolytic immunotherapeutic vaccinia JX-594 in liver cancer*. Nat Med, 2013. 19(3): p. 329-36.
11. Cattaneo, R., *Paramyxovirus entry and targeted vectors for cancer therapy*. PLoS Pathog, 2010. 6(6).
12. Lech, P. J. and S. J. Russell, *Use of attenuated paramyxoviruses for cancer therapy*. Expert Rev Vaccines, 2010. 9(11): p. 1275-302.
13. Sinkovics, J. G. and J. C. Horvath, *Newcastle disease virus (NDV): brief history of its oncolytic strains*. J Clin Virol, 2000. 16(1): p. 1-15.
14. Institute of Laboratory Animal Resources (U.S.). Committee on Infectious Diseases of Mice and Rats, *Infectious diseases of mice and rats*. 1991, Washington, D.C.: National Academy Press. xi, 397 p.
15. Slobod, K. S., et al., *Safety and immunogenicity of intranasal murine parainfluenza virus type 1 (Sendai virus) in healthy human adults*. Vaccine, 2004. 22(23-24): p. 3182-6.
16. Kinoh, H. and M. Inoue, *New cancer therapy using genetically-engineered oncolytic Sendai virus vector*. Front Biosci, 2008. 13: p. 2327-34.
17. Iwadate, Y., et al., *Recombinant Sendai virus vector induces complete remission of established brain tumors through efficient interleukin-2 gene transfer in vaccinated rats*. Clin Cancer Res, 2005. 11(10): p. 3821-7.
18. Tatsuta, K., et al., *Complete elimination of established neuroblastoma by synergistic action of gamma-irradiation and DCs treated with rSeV expressing interferon-beta gene*. Gene Ther, 2009. 16(2): p. 240-51.
19. Yonemitsu, Y., et al., *Immunostimulatory virotherapy using recombinant Sendai virus as a new cancer therapeutic regimen*. Front Biosci, 2008. 13: p. 1892-8.
20. Kurooka, M. and Y. Kaneda, *Inactivated Sendai virus particles eradicate tumors by inducing immune responses through blocking regulatory T cells*. Cancer Res, 2007. 67(1): p. 227-36.
21. Fujihara, A., et al., *Intratumoral injection of inactivated Sendai virus particles elicits strong antitumor activity by enhancing local CXCL10 expression and systemic NK cell activation*. Cancer Immunol Immunother, 2008. 57(1): p. 73-84.
22. Kawaguchi, Y., et al., *Efficient eradication of hormone-resistant human prostate cancers by inactivated Sendai virus particle*. Int J Cancer, 2009. 124(10): p. 2478-87.
23. Saga, K., et al., *Systemic administration of a novel immune-stimulatory pseudovirion suppresses lung metastatic melanoma by regionally enhancing IFN-gamma production*. Clin Cancer Res, 2013. 19(3): p. 668-79.
24. Wheelock, E. F. and J. H. Dingle, *Observations on the Repeated Administration of Viruses to a Patient with Acute Leukemia. A Preliminary Report*. N Engl J Med, 1964. 271: p. 645-51.
25. Krishnamurthy, S., et al., *Differentially regulated interferon response determines the outcome of Newcastle disease virus infection in normal and tumor cell lines*. J Virol, 2006. 80(11): p. 5145-55.
26. Wilden, H., et al., *Expression of RIG-I, IRF3, IFN-beta and IRF7 determines resistance or susceptibility of cells to infection by Newcastle Disease Virus*. Int J Oncol, 2009. 34(4): p. 971-82.
27. Fiola, C., et al., *Tumor selective replication of Newcastle disease virus: association with defects of tumor cells in antiviral defense*. Int J Cancer, 2006. 119(2): p. 328-38.
28. Elankumaran, S., D. Rockemann, and S. K. Samal, *Newcastle disease virus exerts oncolysis by both intrinsic and extrinsic caspase-dependent pathways of cell death*. J Virol, 2006. 80(15): p. 7522-34.
29. Yaacov, B., et al., *Selective oncolytic effect of an attenuated Newcastle disease virus (NDV-HUJ) in lung tumors*. Cancer Gene Ther, 2008. 15(12): p. 795-807.
30. Mansour, M., P. Palese, and D. Zamarin, *Oncolytic specificity of Newcastle disease virus is mediated by selectivity for apoptosis-resistant cells*. J Virol, 2011. 85(12): p. 6015-23.
31. Lazar, I., et al., *The oncolytic activity of Newcastle disease virus NDV-HUJ on chemoresistant primary melanoma cells is dependent on the proapoptotic activity of the inhibitor of apoptosis protein Livin*. J Virol, 2010. 84(1): p. 639-46.
32. Galanis, E., *Therapeutic potential of oncolytic measles virus: promises and challenges*. Clin Pharmacol Ther, 2010. 88(5): p. 620-5.
33. Lin, E. H., et al., *Fusogenic membrane glycoproteins induce syncytia formation and death in vitro and in vivo: a potential therapy agent for lung cancer*. Cancer Gene Ther, 2010. 17(4): p. 256-65.
34. Bateman, A. R., et al., *Viral fusogenic membrane glycoproteins kill solid tumor cells by nonapoptotic mechanisms that promote cross presentation of tumor antigens by dendritic cells*. Cancer Res, 2002. 62(22): p. 6566-78.
35. Higuchi, H., et al., *Viral fusogenic membrane glycoprotein expression causes syncytia formation with bioenergetic cell death: implications for gene therapy*. Cancer Res, 2000. 60(22): p. 6396-402.
36. Ebert, O., et al., *Syncytia induction enhances the oncolytic potential of vesicular stomatitis virus in virotherapy for cancer*. Cancer Res, 2004. 64(9): p. 3265-70.
37. Nakamori, M., et al., *Effective therapy of metastatic ovarian cancer with an oncolytic herpes simplex virus incorporating two membrane fusion mechanisms*. Clin Cancer Res, 2003. 9(7): p. 2727-33.

38. Altomonte, J., et al., *Engineered newcastle disease virus as an improved oncolytic agent against hepatocellular carcinoma*. Mol Ther, 2010. 18(2): p. 275-84.
39. Gainey, M. D., M. J. Manuse, and G. D. Parks, *A hyperfusogenic F protein enhances the oncolytic potency of a paramyxovirus simian virus 5 P/V mutant without compromising sensitivity to type I interferon*. J Virol, 2008. 82(19): p. 9369-80.
40. Bateman, A., et al., *Fusogenic membrane glycoproteins as a novel class of genes for the local and immune-mediated control of tumor growth*. Cancer Res, 2000. 60(6): p. 1492-7.
41. Galanis, E., et al., *Use of viral fusogenic membrane glycoproteins as novel therapeutic transgenes in gliomas*. Hum Gene Ther, 2001. 12(7): p. 811-21.
42. Allen, C., et al., *Adenoviral vectors expressing fusogenic membrane glycoproteins activated via matrix metalloproteinase cleavable linkers have significant antitumor potential in the gene therapy of gliomas*. J Gene Med, 2004. 6(11): p. 1216-27.
43. Hoffmann, D., W. Bayer, and O. Wildner, *In situ tumor vaccination with adenovirus vectors encoding measles virus fusogenic membrane proteins and cytokines*. World J Gastroenterol, 2007. 13(22): p. 3063-70.
44. Hoffmann, D., W. Bayer, and O. Wildner, *Local and distant immune-mediated control of colon cancer growth with fusogenic membrane glycoproteins in combination with viral oncolysis*. Hum Gene Ther, 2007. 18(5): p. 435-50.
45. Dunn, G. P., et al., *A critical function for type I interferons in cancer immunoediting*. Nat Immunol, 2005. 6(7): p. 722-9.
46. Dunn, G. P., C. M. Koebel, and R. D. Schreiber, *Interferons, immunity and cancer immunoediting*. Nat Rev Immunol, 2006. 6(11): p. 836-48.
47. Borden, E. C., et al., *Interferons at age 50: past, current and future impact on biomedicine*. Nat Rev Drug Discov, 2007. 6(12): p. 975-90.
48. Platanias, L. C., *Mechanisms of type-I- and type-II-interferon-mediated signalling*. Nat Rev Immunol, 2005. 5(5): p. 375-86.
49. Cantell, K., et al., *Production of interferon in human leukocytes from normal donors with the use of Sendai virus*. Methods Enzymol, 1981. 78(Pt A): p. 29-38.
50. Hua, J., M. J. Liao, and A. Rashidbaigi, *Cytokines induced by Sendai virus in human peripheral blood leukocytes*. J Leukoc Biol, 1996. 60(1): p. 125-8.
51. Nyman, T. A., et al., *Identification of nine interferon-alpha subtypes produced by Sendai virus-induced human peripheral blood leucocytes*. Biochem J, 1998. 329(Pt 2): p. 295-302.
52. Costas, M. A., et al., *Superinduction of mitogen-stimulated interferon-gamma production and other lymphokines by Sendai virus*. J Interferon Res, 1993. 13(6): p. 407-12.
53. Zeng, J., P. Fournier, and V. Schirrmacher, *Induction of interferon-alpha and tumor necrosis factor-related apoptosis-inducing ligand in human blood mononuclear cells by hemagglutinin-neuraminidase but not F protein of Newcastle disease virus*. Virology, 2002. 297(1): p. 19-30.
54. Takeda, K., T. Kaisho, and S. Akira, *Toll-like receptors*. Annu Rev Immunol, 2003. 21: p. 335-76.
55. Thompson, A. J. and S. A. Locarnini, *Toll-like receptors, RIG-I-like RNA helicases and the antiviral innate immune response*. Immunol Cell Biol, 2007. 85(6): p. 435-45.
56. Homung, V., et al., *5'-Triphosphate RNA is the ligand for RIG-I*. Science, 2006. 314(5801): p. 994-7.
57. Fournier, P., J. Zeng, and V. Schirrmacher, *Two ways to induce innate immune responses in human PBMCs: paracrine stimulation of IFN-alpha responses by viral protein or dsRNA*. Int J Oncol, 2003. 23(3): p. 673-80.
58. Schirrmacher, V. and P. Fournier, *Newcastle disease virus: a promising vector for viral therapy, immune therapy, and gene therapy of cancer*. Methods Mol Biol, 2009. 542: p. 565-605.
59. Wang, B. X., R. Rahbar, and E. N. Fish, *Interferon: current status and future prospects in cancer therapy*. J Interferon Cytokine Res, 2011. 31(7): p. 545-52.
60. Williams, R. F., et al., *Maturation of tumor vasculature by interferon-beta disrupts the vascular niche of glioma stem cells*. Anticancer Res, 2010. 30(9): p. 3301-8.
61. Ikeda, H., L. J. Old, and R. D. Schreiber, *The roles of IFN gamma in protection against tumor development and cancer immunoediting*. Cytokine Growth Factor Rev, 2002. 13(2): p. 95-109.
62. Suzuki, H., et al., *Sendai virus F glycoprotein induces IL-6 production in dendritic cells in a fusion-independent manner*. FEBS Lett, 2008. 582(9): p. 1325-9.
63. Washburn, B. and V. Schirrmacher, *Human tumor cell infection by Newcastle Disease Virus leads to upregulation of HLA and cell adhesion molecules and to induction of interferons, chemokines and finally apoptosis*. Int J Oncol, 2002. 21(1): p. 85-93.
64. Dufour, J. H., et al., *IFN-gamma-inducible protein 10 (IP-10; CXCL10)-deficient mice reveal a role for IP-10 in effector T cell generation and trafficking*. J Immunol, 2002. 168(7): p. 3195-204.
65. Lorence, R. M., P. A. Rood, and K. W. Kelley, *Newcastle disease virus as an antineoplastic agent: induction of tumor necrosis factor-alpha and augmentation of its cytotoxicity*. J Natl Cancer Inst, 1988. 80(16): p. 1305-12.
66. Zorn, U., et al., *Induction of cytokines and cytotoxicity against tumor cells by Newcastle disease virus*. Cancer Biother, 1994. 9(3): p. 225-35.
67. Washburn, B., et al., *TNF-related apoptosis-inducing ligand mediates tumoricidal activity of human monocytes stimulated by Newcastle disease virus*. J Immunol, 2003. 170(4): p. 1814-21.
68. Schirrmacher, V., et al., *Newcastle disease virus activates macrophages for anti-tumor activity*. Int J Oncol, 2000. 16(2): p. 363-73.
69. Vivier, E., et al., *Innate or adaptive immunity? The example of natural killer cells*. Science, 2011.331(6013): p. 44-9.
70. Guo, H., P. Kumar, and S. Malarkannan, *Evasion of natural killer cells by influenza virus*. J Leukoc Biol, 2011.89(2): p. 189-94.
71. Jarahian, M., et al., *Activation of natural killer cells by newcastle disease virus hemagglutinin-neuraminidase*. J Virol, 2009. 83(16): p. 8108-21.
72. Arnon, T. I., et al., *Recognition of viral hemagglutinins by NKp44 but not by NKp30*. Eur J Immunol, 2001.31(9): p. 2680-9.
73. Mandelboim, O., et al., *Recognition of haemagglutinins on virus-infected cells by NKp46 activates lysis by human NK cells*. Nature, 2001. 409(6823): p. 1055-60.
74. Arnon, T. I., et al., *The mechanisms controlling the recognition of tumor- and virus-infected cells by NKp46*. Blood, 2004. 103(2): p. 664-72.
75. Lorence, R. M., et al., *Overview of phase I studies of intravenous administration of PV701, an oncolytic virus*. Curr Opin Mol Ther, 2003. 5(6): p. 618-24.

76. Harada, Y. and Y. Yonemitsu, *Dramatic improvement of DC-based immunotherapy against various malignancies.* Front Biosci, 2011. 16: p. 2233-42.
77. Shibata, S., et al., *Induction of efficient antitumor immunity using dendritic cells activated by recombinant Sendai virus and its modulation by exogenous IFN-beta gene.* J Immunol, 2006. 177(6): p. 3564-76.
78. Okano, S., et al., *Provision of continuous maturation signaling to dendritic cells by RIG-I-stimulating cytosolic RNA synthesis of Sendai virus.* J Immunol, 2011. 186(3): p. 1828-39.
79. Sugiyama, M., et al., *Antagonism of VEGF by genetically engineered dendritic cells is essential to induce antitumor immunity against malignant ascites.* Mol Cancer Ther, 2011. 10(3): p. 540-9.
80. Yoneyama, Y., et al., *Development of immunostimulatory virotherapy using non-transmissible Sendai virus-activated dendritic cells.* Biochem Biophys Res Commun, 2007. 355(1): p. 129-35.
81. Komaru, A., et al., *Sustained and NK/CD4+T cell-dependent efficient prevention of lung metastasis induced by dendritic cells harboring recombinant Sendai virus.* J Immunol, 2009. 183(7): p. 4211-9.
82. Kato, T., et al., *RIG-I helicase-independent pathway in sendai virus-activated dendritic cells is critical for preventing lung metastasis of AT6.3 prostate cancer.* Neoplasia, 2010. 12(11): p. 906-14.
83. Schirrmacher, V., et al., *Virus potentiation of tumor vaccine T-cell stimulatory capacity requires cell surface binding but not infection.* Clin Cancer Res, 1997. 3(7): p. 1135-48.
84. Parato, K. A., et al., *Recent progress in the battle between oncolytic viruses and tumours.* Nat Rev Cancer, 2005. 5(12): p. 965-76.
85. Varki, A., *Glycan-based interactions involving vertebrate sialic-acid-recognizing proteins.* Nature, 2007. 446 (7139): p. 1023-9.
86. Pearlstein, E., et al., *Correlation between spontaneous metastatic potential, platelet-aggregating activity of cell surface extracts, and cell surface sialylation in 10 metastatic-variant derivatives of a rat renal sarcoma cell line.* Proc Natl Acad Sci USA, 1980. 77(7): p. 4336-9.
87. Yogeeswaran, G. and P. L. Salk, *Metastatic potential is positively correlated with cell surface sialylation of cultured murine tumor cell lines.* Science, 1981. 212(4502): p. 1514-6.
88. Fogel, M., P. Altevogt, and V. Schirrmacher, *Metastatic potential severely altered by changes in tumor cell adhesiveness and cell-surface sialylation.* J Exp Med, 1983. 157(1): p. 371-6.
89. Benedetto, A., et al., *Hyposialylation of high-molecular-weight membrane glycoproteins parallels the loss of metastatic potential in wheat-germ agglutinin-resistant Friend leukemia cells.* Int J Cancer, 1989. 43(1): p. 126-33.
90. Collard, J. G., et al., *Cell surface sialic acid and the invasive and metastatic potential of T-cell hybridomas.* Cancer Res, 1986. 46(7): p. 3521-7.
91. Passaniti, A. and G. W. Hart, *Cell surface sialylation and tumor metastasis. Metastatic potential of B16 melanoma variants correlates with their relative numbers of specific penultimate oligosaccharide structures.* J Biol Chem, 1988. 263(16): p. 7591-603.
92. Bresalier, R. S., et al., *Cell surface sialoprotein alterations in metastatic murine colon cancer cell lines selected in an animal model for colon cancer metastasis.* Cancer Res, 1990. 50(4): p. 1299-307.
93. Komminoth, P., et al., *Polysialic acid of the neural cell adhesion molecule in the human thyroid: a marker for medullary thyroid carcinoma and primary C-cell hyperplasia. An immunohistochemical study on 79 thyroid lesions.* Am J Surg Pathol, 1994. 18(4): p. 399-411.
94. Sata, T., et al., *Expression of alpha 2,6-linked sialic acid residues in neoplastic but not in normal human colonic mucosa. A lectin-gold cytochemical study with Sambucus nigra and Maackia amurensis lectins.* Am J Pathol, 1991. 139(6): p. 1435-48.
95. Pousset, D., et al., *Increased alpha2, 6 sialylation of N-glycans in a transgenic mouse model of hepatocellular carcinoma.* Cancer Res, 1997. 57(19): p. 4249-56.
96. Fernandez-Rodriguez, J., et al., *Immunohistochemical analysis of sialic acid and fucose composition in human colorectal adenocarcinoma.* Tumour Biol, 2000. 21(3): p. 153-64.
97. Dall'Olio, F., et al., *Beta-galactoside alpha2,6 sialyltransferase in human colon cancer: contribution of multiple transcripts to regulation of enzyme activity and reactivity with Sambucus nigra agglutinin.* Int J Cancer, 2000. 88(1): p. 58-65.
98. Takano, R., E. Muchmore, and J. W. Dennis, *Sialylation and malignant potential in tumour cell glycosylation mutants.* Glycobiology, 1994. 4(5): p. 665-74.
99. Vierbuchen, M. J., et al., *Quantitative lectin-histochemical and immunohistochemical studies on the occurrence of alpha(2,3)- and alpha(2,6)-linked sialic acid residues in colorectal carcinomas. Relation to clinicopathologic features.* Cancer, 1995. 76(5): p. 727-35.
100. Hsu, C. C., et al., *Soyasaponin-I-modified invasive behavior of cancer by changing cell surface sialic acids.* Gynecol Oncol, 2005. 96(2): p. 415-22.
101. Chang, W. W., et al., *Soyasaponin I decreases the expression of alpha2,3-linked sialic acid on the cell surface and suppresses the metastatic potential of B16F10 melanoma cells.* Biochem Biophys Res Commun, 2006. 341(2): p. 614-9.
102. Chiang, C. H., et al., *A novel sialyltransferase inhibitor AL10 suppresses invasion and metastasis of lung cancer cells by inhibiting integrin-mediated signaling.* J Cell Physiol, 2010. 223(2): p. 492-9.
103. Vierbuchen, M., et al., *Native and sialic acid masked Lewis(a) antigen reactivity in medullary thyroid carcinoma. Distinct tumour-associated and prognostic relevant antigens.* Virchows Arch, 1994.424(2): p. 205-11.
104. Cohen, M., et al., *Sialylation of 3-methylcholanthrene-induced fibrosarcoma determines antitumor immune responses during immunoediting.* J Immunol, 2010. 185 (10): p. 5869-78.
105. Kingsbury, D. W., *The paramyxoviruses.* 1st ed. ed. 1991: Springer.
106. Enders, G., *Paramyxoviruses.*
107. Knipe, D. M., in *Fields virology.* 2007, Lippincott Williams & Wilkins
108. Powell, L. D., S. W. Whiteheart, and G. W. Hart, *Cell surface sialic acid influences tumor cell recognition in the mixed lymphocyte reaction.* J Immunol, 1987. 139(1): p. 262-70.
109. Tyagarajan, K., J. G. Forte, and R. R. Townsend, *Exoglycosidase purity and linkage specificity: assessment using oligosaccharide substrates and high-pH anion-exchange chromatography with pulsed amperometric detection.* Glycobiology, 1996. 6(1): p. 83-93.
110. Drzeniek, R. and A. Gauhe, *Differences in substrate specificity of myxovirus neuraminidases.* Biochem Biophys Res Commun, 1970. 38(4): p. 651-6.

111. Brostrom, M. A., G. Bruening, and R. A. Bankowski, *Comparison of neuraminidases of paramyxoviruses with immunologically dissimilar hemagglutinins.* Virology, 1971. 46(3): p. 856-65.

The invention claimed is:

1. A method of treating cancer that includes administering to a human or animal patient in need thereof a composition containing an isolated, native, biologically active virus Sendai strain deposited at ATCC under Accession Number PTA-13024 or under Accession Number PTA-121432 and a pharmaceutically acceptable carrier.

2. The method of claim 1, wherein the composition is administered intratumorally.

3. The method of claim 1, wherein the composition is administered intradermally, subcutaneously, intramuscularly or intravenously.

4. The method of claim 1 further including administering to the patient X-ray inactivated cells obtained by dispersion of the patient's tumor tissues.

5. The method of claim 1 further including administering to the patient X-ray inactivated cells of an immunogenic cell line.

6. The method of claim 1 further including administering to the patient chick embryo cells, wherein replication of the virus is possible in the chick embryo cells inside the patient's body.

7. The method of claim 1 further including administering to the patient chick embryo cells and X-ray inactivated cells obtained by dispersion of the patient's tumor tissues, wherein replication of the virus is possible in the chick embryo cells inside the patient's body.

8. The method of claim 1 further including administering to the patient chick embryo cells and X-ray inactivated cells of an immunogenic cell line, wherein replication of the virus is possible in the chick embryo cells inside the patient's body.

9. The method of any one of claims 1-8, wherein 1 to 12 injections of the composition are administered to a patient with 7-10 day intervals.

10. A pharmaceutical composition for therapeutic use containing isolated, native, biologically active virus Sendai strain deposited at ATCC under Accession Number PTA-13024 or under Accession Number PTA-121432 and pharmaceutically acceptable carrier.

11. The composition of claim 10 further containing X-ray inactivated cells obtained by dispersion of tumor tissues obtained from a human or animal cancer patient.

12. The composition of claim 10 further containing X-ray inactivated cells of an immunogenic cell line.

13. The composition of claim 10 further containing chick embryo cells, wherein, upon administration of the composition to a human or animal cancer patient, replication of the virus in the chick embryo cells is possible inside the patient's body.

14. The composition of claim 10 further containing chick embryo cells and X-ray inactivated cells obtained by dispersion of tumor tissues obtained from a human or animal cancer patient, wherein, upon administration of the composition to a human or animal cancer patient, replication of the virus in the chick embryo cells is possible inside the patient's body.

15. The composition of claim 10 further containing chick embryo cells and X-ray inactivated cells of an immunogenic cell line, wherein, upon administration of the composition to a human or animal cancer patient, replication of the virus in the chick embryo cells is possible inside the patient's body.

16. A pharmaceutical composition for therapeutic use containing isolated, genetically engineered, biologically active virus Sendai strain prepared on the basis of the viral material deposited at ATCC under Accession Number PTA-13024 or under Accession Number PTA-121432 and pharmaceutically acceptable carrier.

* * * * *